United States Patent
Chang et al.

(10) Patent No.: US 7,074,840 B2
(45) Date of Patent: Jul. 11, 2006

(54) LIGHT ADJUSTABLE LENSES CAPABLE OF POST-FABRICATION POWER MODIFICATION VIA MULTI-PHOTON PROCESSES

(75) Inventors: Shiao H. Chang, Pasadena, CA (US); Robert H. Grubbs, South Pasadena, CA (US); Julia A. Kornfield, Pasadena, CA (US); Axel Brait, Pasadena, CA (US)

(73) Assignee: Calhoun Vision, Pasadena, CA (US)

( * ) Notice: Subject to any disclaimer, the term of this patent is extended or adjusted under 35 U.S.C. 154(b) by 75 days.

(21) Appl. No.: 10/914,378

(22) Filed: Aug. 9, 2004

(65) Prior Publication Data

US 2005/0027031 A1    Feb. 3, 2005

Related U.S. Application Data

(63) Continuation-in-part of application No. 10/324,540, filed on Dec. 19, 2002.

(60) Provisional application No. 60/493,746, filed on Aug. 8, 2003.

(51) Int. Cl.
*G03C 1/73* (2006.01)
*C08L 33/04* (2006.01)
*C08F 2/50* (2006.01)

(52) U.S. Cl. .......................... 522/65; 522/63; 522/172; 522/173; 522/904; 359/234; 252/600

(58) Field of Classification Search ................... 522/65, 522/63, 172, 173, 904, 116, 117, 121, 153, 522/136, 137, 142; 252/600
See application file for complete search history.

(56) References Cited

U.S. PATENT DOCUMENTS

| | | | |
|---|---|---|---|
| 3,985,566 A * | 10/1976 | Buhr et al. | 430/287.1 |
| 4,391,963 A * | 7/1983 | Shirahata | 528/37 |
| 4,477,326 A * | 10/1984 | Lin | 522/21 |
| 4,534,838 A * | 8/1985 | Lin et al. | 522/33 |
| 4,921,589 A * | 5/1990 | Yates et al. | 204/157.5 |
| 5,770,737 A | 6/1998 | Reinhardt et al. | |
| 6,100,405 A * | 8/2000 | Reinhardt et al. | 548/160 |
| 6,267,913 B1 * | 7/2001 | Marder et al. | 252/582 |
| 6,300,502 B1 * | 10/2001 | Kannan et al. | 548/156 |
| 6,316,153 B1 | 11/2001 | Goodman et al. | |
| 6,376,568 B1 * | 4/2002 | Baudin et al. | 522/6 |
| 6,402,037 B1 | 6/2002 | Prasad | |
| 6,555,682 B1 | 4/2003 | Kannan | |
| 6,566,529 B1 | 5/2003 | Kim | |
| 6,608,228 B1 * | 8/2003 | Cumpston et al. | 564/308 |
| 6,730,793 B1 * | 5/2004 | Kannan et al. | 548/150 |
| 2002/0185634 A1 | 12/2002 | Marder | |
| 2003/0052311 A1* | 3/2003 | Ingaaki et al. | 252/600 |
| 2003/0236425 A1* | 12/2003 | Herr et al. | 556/443 |
| 2004/0068023 A1* | 4/2004 | Leatherdale et al. | 522/2 |

FOREIGN PATENT DOCUMENTS

WO     WO 00/68218     * 11/2000

* cited by examiner

*Primary Examiner*—Susan Berman
(74) *Attorney, Agent, or Firm*—Fulbright & Jaworski LLP

(57) ABSTRACT

The invention relates to novel photoinitiators and their use in light adjustable compositions. The initiatives comprise two or more multiphoton chromophores linked by a bridging compound. The bridging compound consists of a material that is compatible with the base material of the light adjustable composition. The novel photoinitiator permit the readjustment of light adjustable material without the need for significant amounts of photoabsorbers.

11 Claims, No Drawings

LIGHT ADJUSTABLE LENSES CAPABLE OF POST-FABRICATION POWER MODIFICATION VIA MULTI-PHOTON PROCESSES

CROSS-REFERENCE TO RELATED APPLICATIONS

This Application claims the benefit of the priority date of U.S. application Ser. No. 60/493,746 filed Aug. 8, 2003 and is also a continuation in part of U.S. application Ser. No. 10/324,540 filed Dec. 19, 2002.

STATEMENT REGARDING FEDERALLY SPONSORED RESEARCH OR DEVELOPMENT

Not applicable.

REFERENCE TO A COMPACT DISK APPENDIX

Not applicable.

TECHNICAL FIELD

The invention relates to novel photoinitiator compositions and their use in light adjustable compositions. These novel initiators permit the adjustment of light adjustable compositions using visible light and provide a material that is compatible with the base material and provides optical clarity.

BACKGROUND OF THE INVENTION

Approximately two million cataract surgery procedures are performed in the United States annually. The procedure generally involves making an incision in the anterior lens capsule to remove the cataractous crystalline lens and implanting an intraocular lens in its place. The power of the implanted lens is selected (based upon pre-operative measurements of ocular length and corneal curvature) to enable the patient to see without additional corrective measures (e.g., glasses or contact lenses). Unfortunately, due to errors in measurement, and/or variable lens positioning and wound healing, about half of all patients undergoing this procedure will not enjoy optimal vision without correction after surgery. Brandser et al., *Acta Ophthalmol Scand* 75:162–165 (1997); Oshika et al., *J Cataract Refract Surg* 24:509–514 (1998). Because the power of prior art intraocular lenses generally cannot be adjusted once they have been implanted, the patient typically must choose between replacing the implanted lens with another lens of a different power or be resigned to the use of additional corrective lenses such as glasses or contact lenses. Since the benefits typically do not outweigh the risks of the former, it is almost never done.

One solution to this problem has been the development of light adjustable intraocular lenses such as those disclosed in U.S. Pat. No. 6,450,642. The lenses described therein are formed from a polymer matrix having photopolymerizable macromers dispersed therein. The photopolymerization of the macromers induces changes in one or more properties of the lens including changes in the optical properties. The lenses, however, require that the macromers be fully consumed in a "lock-in" step preventing unintentional changes in the lens by exposure to UV or ambient light. This exhaustion of the macromers prevents further adjustments to the lens after the initial series of corrections.

A potential method for eliminating the need for a lock-in step is through the use of two photon initiators such as those described and disclosed in U.S. Pat. Nos. 6,267,913; 6,316,153; 6,402,037; 6,555,682; and 6,566,529 as well as published U.S. applications 2002/0185634 and 2003/0052311. The chromophores described in these applications require the use of high intensity light to trigger a release of energy sufficient to initiate a polymerization reaction. While these materials can be used, they are generally not compatible with the materials used to make light adjustable lenses such as siloxanes or acrylates. This incompatibility reduces the optical clarity of the materials and can result in the leaching of the initiators from the lens. This makes these initiators unacceptable for use in optical elements especially contact lenses or intraocular lenses.

It is therefore desirable to provide a photoinitiator that is triggered by light with an intensity greater than ambient light that is compatible with the base material of the light adjustable composition or article.

BRIEF SUMMARY OF THE INVENTION

The invention comprises a photoinitiating composition that is compatible with the base material used to make the light adjustable compositions or articles. The photoinitiators of the invention comprise the general formula:

$$A\text{-}B\text{-}A^1$$

wherein B is a bridging compound comprising a monomer, homopolymer or copolymer of a similar nature to the base material of the light adjustable composition and A and $A^1$, which can be the same or different, comprising multi-photon chromophores.

In one embodiment, the bridging compound comprises siloxane or acrylate moieties depending upon the nature of the base material. For example, in the case of an intraocular lens made from polysiloxanes, B is preferably also a siloxane and when the lens is a polyacrylate, then B is an acrylate.

In one embodiment, the chromophore absorbs light via two-photon absorption in the range of 400–1500 nm, preferably 400 to 800 nm, most preferred 500 to 700 nm. Owning to the nature of the chromophores, the light must be at an intensity in excess of that encountered from ambient light and at a high enough intensity to enable the simultaneous absorption of two or more photons during irradiation.

The novel photoinitiators of the present invention are particularly useful as the photoinitiator for light adjustable optical elements. Because the photoinitiators are triggered by visible light at intensities significantly greater than ambient light (e.g. normal sunlight), use of these novel photoinitiators permits the manufacture and implementation of light adjustable optical elements which do not require a lock-in-step to prevent unwanted changes in the optical element and can be readjusted one or more times over the life of the optical element.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

The novel photoinitiators of the invention use light in the visible light wavelengths but require an intensity of light much greater than that encountered in ambient light. Thus they can be activated using lasers or other light sources, which provide sufficient intensity but do not require the use of ultraviolet light. The presence of a bridging compound similar in composition to the base material used to make the light adjustable article, improves compatibility, helps ensure optical clarity and prevents leaching of the photoinitiator to the aqueous environment of the eye. The use of the photoinitiator, which is activated by high intensity light, permits the fabrication of light adjustable materials whose properties can be changed several times over a prolonged period of time. The use of the novel photoinitiators of the invention will also permit the fabrication of blue light absorbing light adjustable lenses capable of filtering out blue light to protect lipoftiscin filled RPE (retinal pigment epithelium) cells against blue light damage.

The novel photoinitiators of the invention have the general formula:

A-B-A$^1$ wherein A is a multiphoton chromophores and A$^1$ is a non-chromophore end-functionality or a multiphoton chromophore that is the same as A or different and B is a bridging compound comprising a monomer, homopolymer or copolymer having a composition similar to the base material. For example, where the base material comprises polysiloxanes, B will have the general formula:

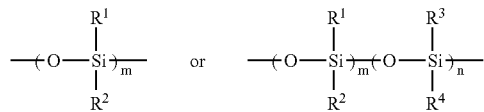

wherein m and n are integers greater than or equal to 1, preferably greater than or equal to 5 and less than or equal to 10. R$^1$, R$^2$, R$^3$ and R$^4$ are independently selected from the group consisting of hydrogen, alkyl, halogenated alkyl, aryl, halogenated aryl and arylalkyl moieties.

Similarly, where the base material is a polyacrylate, B will have the general formula:

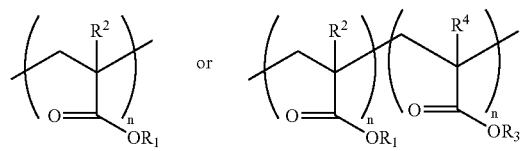

wherein m, n, R$^1$, R$^2$, R$^3$ and R$^4$ are as defined above.

The multiphoton chromophore elements A and A$^1$ are preferably two photon chromophores that are capable of using visible light to initiate a polymerization reaction via a multiphoton absorption. Typically, these chromophores absorb light in the range of 200–1500 nm with from 400–900 nm preferred for 2-photon absorption. As used herein, the term high intensity light means light at an intensity greater than the intensity encountered under ambient conditions and sufficient to trigger photopolymerization. For example, in one embodiment, the initiator is triggered by light at about 532 nm at a pulse duration of about 0.5 ns with a maximum pulse energy of about 4 µJ. The chromophores useful in the practice of the invention are modified to permit bonding to the bridging moiety. This is typically done through the addition of one or more vinyl or allyl groups on the chromophore but any reactive group which can bond to a group on the bridging compound can be used.

When the chromophore has been modified by the addition of a vinyl group, the chromophore is bonded to the bridging compound by a vinyl-hydride reaction in the case of the silicone bridge and, for example, ATRP (atom transfer radical polymerization) endcapping in the case of an acrylate bridge. While this will generally occur at a terminal hydride for a silicone bridge, the reaction can occur at any available hydride. Thus the invention is not limited to photoinitiators where the chromophore is attached at the end of the bridging compound. Analogous the chromophore can be attached at any place along the acrylate bridge, including at the ends of the bridging acrylate.

One group of chromophores useful in the practice of the invention have the general formula:

D-π-D wherein D is a tertiary amino electron-donor group and π is a conjugated bridge. For example, the π can be selected from the group consisting of fluorene, diphenylpolyene, bis-(styryl)benzene, bis(phenylbutadienyl)benzene and bis-(styryl)benzene.

One particularly useful chromophore has the general formula:

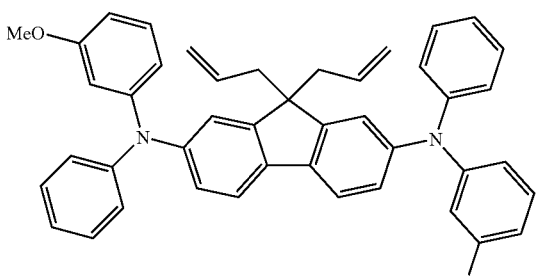

This chromophore is prepared by the addition of two allyl groups to dibromofluorene followed by palladium coupling with 3-methoxydiphenyl-amine in the manner shown below:

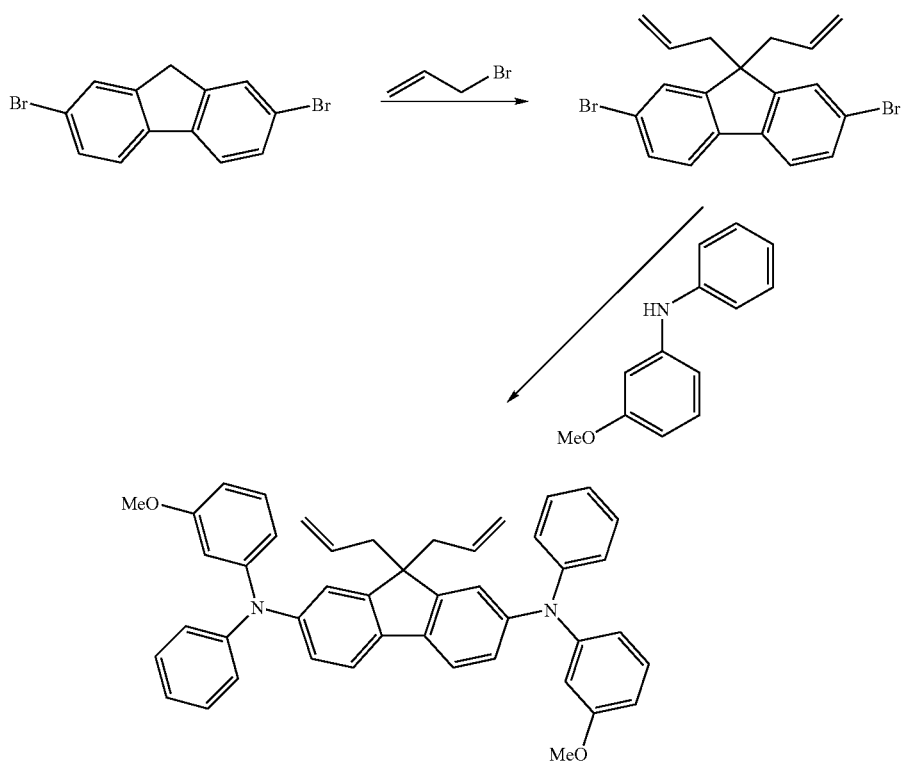

As shown in the structure above, the chromophore has two available allyl groups. These groups can react with a hydride group on the siloxane moiety or via ATRP endcapping with the radical end of an acrylate moiety using techniques well known in the art to yield a structure such as:

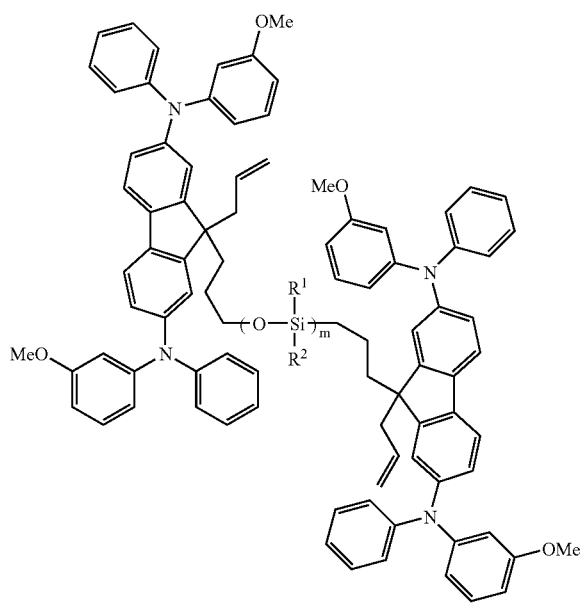

The resulting photoinitiator is triggered by exposure to light in the range of 400–900 nm but is not activated by light in the intensity of ambient light.

As discussed above, the novel photoinitiators of the invention are particularly useful in light adjustable compositions or articles particularly light adjustable optical elements.

The light adjustable article or composition generally comprises a base material which is generally formed from a polymer matrix and photopolymerizable macromers which are incorporated into but not bound to the base material. The novel photoinitiators are also incorporated into the base material such that they can initiate the photopolymerization of the macromers by multiphoton absorption upon exposure to light of sufficient intensity and in the proper wavelength. The photopolymerization of the macromers induces changes in the properties of the composition. For example, in the case of an optical element, the photopolymerization of the macromer can cause changes in the refractive index of the base material. The photopolymerization can also cause changes in the shape of the base material. This may also affect the optical properties of the material.

The invention also relates to optical elements whose optical properties can be continuously modified or adjusted over its useful life. This adjustment is accomplished in a self-contained system that is without the addition or removal of material from the element. The use of the novel photoinitiators of the present invention permits the readjustment of the optical elements over time. This also eliminates the need for a "lock-in" step to prevent unwanted changes in the optical element due to exposure to ambient light.

Typical optical elements within the scope of the invention include data storage elements, including compact disks, digital video disks; lenses, including but not limited to spectacle lenses; contact lenses, intraocular lenses; mirrors, prisms, and the like. In the preferred embodiment, the optical element is an intraocular lens.

The optical element is typically prepared from a first polymer matrix which gives shape to the element as well as many of its physical properties such as hardness, flexibility and the like.

The optical element also contains a macromer dispersed therein. This macromer may be a single compound or a combination of compounds that is capable of stimulus-induced polymerization, preferably photopolymerization.

The nature of the first polymer matrix and the macromer will vary depending upon the end use contemplated for the optical element. However, as a general rule, the first polymer matrix and the macromer are selected such that the components that comprise the macromer are capable of diffusion within the first polymer matrix. Put another way, a loose first polymer matrix will tend to be paired with larger macromer components and a tight first polymer matrix will tend to be paired with smaller macromer components.

Upon exposure to an appropriate energy (e.g., heat or light), the macromer typically forms a second polymer matrix in the exposed region of the optical element. The presence of the second polymer matrix changes the material characteristics of this portion of the optical element to modulate its refraction capabilities. In general, the formation of the second polymer matrix typically increases the refractive index of the affected portion of the optical element. After exposure, the macromer in the unexposed region will migrate into the exposed region over time. The amount of macromer migration into the exposed region is time dependent and may be precisely controlled. If enough time is permitted, the macromer components will re-equilibrate and redistribute throughout optical element (i.e., the first polymer matrix, including the exposed region). When the region is re-exposed to the energy source, the macromer that has since migrated into the region (which may be less than if the macromer were allowed to re-equilibrate) polymerizes to further increase the formation of the second polymer matrix. This process (exposure followed by an appropriate time interval to allow for diffusion) may be repeated until the exposed region of the optical element has reached the desired property (e.g., power, refractive index, or shape). At this point, because the novel photoinitiator require the use of light at an intensity above ambient conditions, no further polymerization occurs until the element is exposed to the specific wave length and intensity. Thus, in the case of an intraocular lens, the lens may be exposed to natural light and the like without further changes in the lens. If adjustments are needed because of aging or changes in the patient's health, for example, the lens can be adjusted by exposure to an appropriate energy source.

The first polymer matrix is a covalently or physically linked structure that functions as an optical element and is formed from a first polymer matrix composition ("FPMC"). In general, the first polymer matrix composition comprises one or more monomers that upon polymerization will form the first polymer matrix. The first polymer matrix composition optionally may include any number of formulation auxiliaries that modulate the polymerization reaction or improve any property of the optical element. Illustrative examples of suitable FPMC monomers include acrylics, methacrylates, phosphazenes, siloxanes, vinyls, homopolymers and copolymers thereof. As used herein, a "monomer" refers to any unit (which may itself either be a homopolymer or copolymer)$_2$ which may be linked together to form a polymer containing repeating units of the same. If the FPMC monomer is a copolymer, it may be comprised of the same type of monomers (e.g., two different siloxanes) or it may be comprised of different types of monomers (e.g., a siloxane and an acrylic).

In one embodiment, the one or more monomers that form the first polymer matrix are polymerized and cross-linked in the presence of the macromer. In another embodiment, polymeric starting material that forms the first polymer matrix is cross-linked in the presence of the macromer. Under either scenario, the macromer components must be compatible with and not appreciably interfere with the formation of the first polymer matrix. Similarly, the formation of the second polymer matrix should also be compatible with the existing first polymer matrix. Put another way, the first polymer matrix and the second polymer matrix should not phase separate and light transmission by the optical element should be unaffected.

As described previously, the macromer may be a single component or multiple components so long as: (i) it is compatible with the formation of the first polymer matrix; (ii) it remains capable of stimulus-induced polymerization after the formation of the first polymer matrix: and (iii) it is freely diffusible within the first polymer matrix. In preferred embodiments, the stimulus-induced polymerization is photo-induced polymerization.

In general, there are two types of intraocular lenses ("IOLs"). The first type of an intraocular lens replaces the eye's natural lens. The most common reason for such a procedure is cataracts. The second type of intraocular lens supplements the existing lens and functions as a permanent corrective lens. This type of lens (sometimes referred to as a phakic intraocular lens) is implanted in the anterior or posterior chamber to correct any refractive errors of the eye. In theory, the power for either type of intraocular lenses required for emmetropia (i.e., perfect focus on the retina from light at infinity) can be precisely calculated. However, in practice, due to errors in measurement of corneal curvature, and/or variable lens positioning and wound healing, it is estimated that only about half of all patients undergoing IOL implantation will enjoy the best possible vision without the need for additional correction after surgery. Because prior art IOLs are generally incapable of post-surgical power modification, the remaining patients must resort to other types of vision correction such as external lenses (e.g. glasses or contact lenses) or cornea surgery. The need for these types of additional corrective measures is obviated with the use of the intraocular lenses of the present invention.

The inventive intraocular lens comprises a first polymer matrix and a macromer dispersed therein. The first polymer matrix and the macromer are as described above with the additional requirement that the resulting lens be biocompatible.

Illustrative examples of a suitable first polymer matrix include: polyacrylates such as polyalkyl acrylates and polyhydroxyalkyl acrylates; polymethacrylates such as polymethyl methacrylate ("PMMA"), a polyhydroxyethyl methacrylate ("PHEMA"), and polyhydroxypropyl methacrylate ("HPMA"); polyvinyls such as polystyrene and polyvinylpyrrolidone ("NVP"); polysiloxanes such as polydimethylsiloxane; polyphosphazenes, and copolymers of thereof. U.S. Pat. No. 4,260,725 and patents and references cited therein (which are all incorporated herein by reference) provide more specific examples of suitable polymers that may be used to form the first polymer matrix.

In preferred embodiments, the first polymer matrix generally possesses a relatively low glass transition temperature ("$T_g$") such that the resulting IOL tends to exhibit fluid-like and/or elastomeric behavior. In applications where flexibility is important (e.g., intraocular lenses or contact lenses), the $T_g$ will generally be less than 25° C. preferably less than 20° C. Where rigidity is important, the $T_g$ will be much higher, e.g., 25° C. to 50° C.

The first polymer matrix is typically formed by cross-linking one or more polymeric starting materials wherein each polymeric starting material includes at least one cross-linkable group. Illustrative examples of suitable cross-linkable groups include but are not limited to hydride, acetoxy, alkoxy, amino, anhydride, aryloxy, carboxy, enoxy, epoxy, halide, isocyano, olefinic, and oxine. In more preferred embodiments, each polymeric starting material includes terminal monomers (also referred to as endcaps) :that are either the same or different from the one or more monomers that comprise the polymeric starting material but include at least one cross-linkable group. In other words, the terminal monomers begin and end the polymeric starting material and include at least one cross-linkable group as part of its structure. Although it is not necessary for the practice of the present invention, the mechanism for cross-linking the polymeric starting material preferably is different than the mechanism for the stimulus-induced polymerization of the components that comprise the macromer. For example, if the macromer is polymerized by photo-induced polymerization, then it is preferred that the polymeric starting materials have cross-linkable groups that are polymerized by any mechanism other than photo-induced polymerization.

An especially preferred class of polymeric starting materials for the formation of the first polymer matrix is polysiloxanes (also known as "silicones") endcapped with a terminal monomer which includes a cross-linkable group selected from the group of unsaturated alkyl such as vinyl. Because silicone IOLs tend to be flexible and foldable, generally smaller incisions may be used during the IOL implantation procedure. An example of an especially preferred polymeric starting material is bis(vinyldimethylsilyl)-polydimethysiloxane (which is polydimethylsiloxane that is endcapped with a vinyldimethylsilyl terminal monomer).

The macromer that is used in fabricating IOLs is as described above except that it has the additional requirement of biocompatibility. The macromer is capable of stimulus-induced polymerization and may be a single component or multiple components so long as: (i) it is compatible with the formation of the first polymer matrix; (ii) it remains capable of stimulus-induced polymerization after the formation of the first polymer matrix; and (iii) it is freely diffusable within the first polymer matrix. In general, the same type of monomers that is used to form the first polymer matrix-may be used as a component of the macromer. However, because of the requirement that the macromer monomers must be diffusable within the first polymer matrix, the macromer monomers generally tend to be smaller (i.e., have lower molecular weights) than the monomers, which form the first polymer matrix. In addition to the one or more monomers, the macromer may include other components such as initiators and sensitizers that facilitate the formation of the second polymer matrix.

Because of the preference for flexible and foldable IOLs, an especially preferred class of macromer monomers is polysiloxanes endcapped with a terminal siloxane moiety that includes a photopolymerizable group. An illustrative representation of such a monomer is:

X-Y-X¹ wherein Y is a siloxane which may be a monomer, a homopolymer or a copolymer formed from any number of siloxane units, and X and X¹ may be the same or different and are each independently a terminal siloxane moiety that includes a photopolymerizable group. Illustrative examples of Y include:

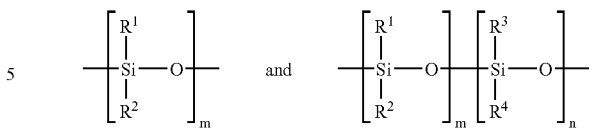

wherein m and n are independently each an integer and $R^1$, $R^2$, $R^3$, and $R^4$, are independently each hydrogen, alkyl (primary, secondary, tertiary, cyclo), aryl, or heteroaryl. In preferred embodiments, $R^1$, $R^2$, $R^3$, and $R^4$, is a $C_1$–$C_{10}$ alkyl or phenyl. Because macromer monomers with a relatively high aryl content have been found to produce larger changes in the refractive index of the inventive lens, it is generally preferred that at least one of $R^1$, $R^2$, $R^3$, and $R^4$ is an aryl, particularly phenyl. In more preferred embodiments. $R^1$, $R^2$, $R^3$ are the same and are methyl, ethyl or propyl and $R^4$ is phenyl.

Illustrative examples of X and $X^1$ (or $X^1$ and X depending on how the macromer polymer is depicted) are:

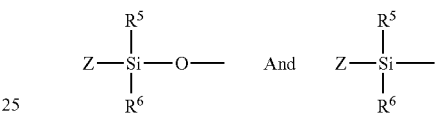

respectively wherein $R^5$ and $R^6$ are independently each hydrogen, alkyl, aryl, or heteroaryl; and Z is a photopolymerizable group.

In preferred embodiments $R^1$ and $R^6$ are independently each a $C_1$ and $C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, $R^5$ and $R^6$ is methyl, ethyl, or propyl and Z is a photopolymerizable group that includes an acrylate or methacrylate moiety.

In especially preferred embodiments, an macromer monomer is of the following formula:

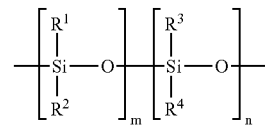

wherein X and $X^1$ are the same and $R^1$, $R^2$, $R^3$, and $R^4$ are as defined previously. Illustrative examples of such macromer monomers include dimethylsiloxane-diphenylsiloxane copolymer endcapped with a vinyl dimethylsilyl group; dimethylsiloxane-methylphenylsiloxane copolymer endcapped with a methacryloxypropyl dimethylsilyl group; and dimethylsiloxane endcapped with a methacryloxypropyldimethylsilyl group. Although any suitable method may be used, a ring-opening reaction of one or more cyclic siloxanes in the presence of triflic acid has been found to be a particularly efficient method of making one class of inventive macromer monomers. Briefly, the method comprises contacting a cyclic siloxane with a compound of the formula:

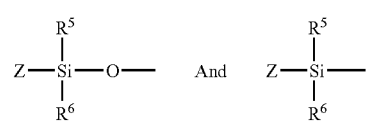

in the presence of triflic acid wherein $R^5$, $R^6$, and Z are as defined previously. The cyclic siloxane may be a cyclic siloxane monomer, homopolymer, or copolymer. Alternatively, more than one cyclic siloxane may be used. For example, a cyclic dimethylsiloxane tetramer and a cyclic methyl-phenylsiloxane trimer are contacted with bis-methacryloxypropyltetramethyldisiloxane in the presence of triflic acid to form a dimethyl-siloxane methyl-phenylsiloxane copolymer that is endcapped with a methacryloxylpropyl-dimethylsilane group, an especially preferred macromer monomer.

Alternatively, the macromer of the invention may comprise multifunctional acrylate based monomers having the general formula:

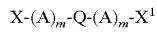

or

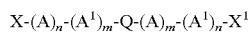

wherein Q is an acrylate based compound used to create the acrylate monomer; A and $A^1$ are the same or different and have the general structure:

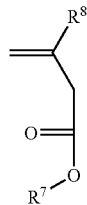

wherein $R^7$ and $R^8$ are alkly, haloalkyl, aryl, haloaryl, and X and $X^1$ contain moieties capable of stimulus induced polymerization, preferably photopolymerizable groups and N and M are integers.

In one embodiment the macromer has the general structure

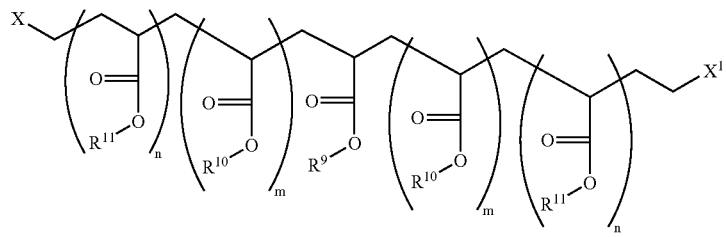

wherein $R^9$, $R^{10}$ and $R^{11a}$ are independently selected from the group consisting of alkyls, haloalkyls, aryls, and haloaryls and n and m are integers and X and $X^1$ are as defined above.

A key advantage of the optical element of the present invention is that an element property may be modified post-fabrication. In the case of an IOL, for example, the modification may be made after implantation within the eye. For example, any errors in the power calculation due to imperfect corneal measurements and/or variable lens positioning and wound healing may be modified in a post surgical outpatient procedure. Additionally, corrections due to physical changes in the patient over time can also be made.

In addition to the change in the element's refractive index, the stimulus-induced formation of the second polymer matrix has been found to affect the element's power by altering the shape of the element in a predictable manner. For example, in one embodiment, formation of the second polymer matrix changes the thermodynamic equilibrium in this element. This in turn promotes the migration of the macromer, which in turn can cause a change in the curvature of the lens. As a result, both mechanisms may be exploited to modulate an IOL property, such as power, after it has been implanted within the eye. In general, the method for implementing an inventive optical element having a first polymer matrix and a macromer dispersed therein comprises:

(a) exposing at least a portion of the optical element to a stimulus whereby the stimulus induces the polymerization of the macromer. This step may be skipped if the element possesses the desired initial properties;

(b) determining that a change in optical properties is required or desired;

(c) exposing or reexposing at least a portion of the element to a stimulus whereby the stimulus induces polymerization of the macromer to cause a change in optical properties of the element;

(d) waiting for a period of time;

(e) evaluating the performance of the element.

After exposure to an external stimulus, the element may need to be re-exposed to stimulus until the desired optical properties are achieved.

In another embodiment, wherein an optical element's properties need to be modified, a method for modifying the element comprises:

(a) exposing a first portion of the optical element to a stimulus whereby the stimulus induces the polymerization of the macromer; and (b) exposing a second portion of the lens to the stimulus.

The first element portion and the second element portion represent different regions of the lens although they may overlap. Optionally, the method may include an interval of time between the exposures of the first element portion and the second element portion. In addition, the method may further comprise re-exposing the first element portion and/or the second element portion any number of times (with or without an interval of time between exposures) or may further comprise exposing additional portions of the element (e.g., a third element portion, a fourth element portion, etc.).

In general, the location of the one or more exposed portions will vary depending on the type of refractive error being corrected. For example, in one embodiment, the exposed portion of the IOL is the optical zone, which is the center region of the lens (e.g., between about 4 mm and about 5 mm in diameter). Alternatively, the one or more exposed lens portions may be along IOL's outer rim or along a particular meridian. In another embodiment, different regions of a spectacle lens can be exposed to a stimulus thereby creating a bifocal spectacle lens. In preferred embodiments, the stimulus is light. In more preferred embodiments, the light is from a laser source.

As noted above, those adjustments can be made during the course of the initial adjustment or can occur weeks or years later. Thus, as the needs of the users change over time, the optical properties can be adjusted without the need for surgery or the like.

The readjustable properties of the optical element can also lead to novel data storage devices. By controlling the region where the second polymer matrix is found, it is possible to record data in three dimensions and then add or change the data stored at a later time.

As discussed above, the multiphoton initiators of the present invention require the use of light at intensities above ambient to induce or initiate the photopolymerization reaction. Thus the reaction will generally not occur at ambient conditions. In addition, when the intense light is stopped, the polymerization reaction stops. Thus it is possible to photopolymerize only a portion of the macromer present in the base material leaving a significant amount of material available for further polymerization at a later time. This time can be as short as a few days or hours or as long as weeks, months or years. Thus the readjustment can be done to fine tune the initial adjustment made or it can be a complete change in characteristics of the material. For example, in the case of an intraocular lens, the lens can be first adjusted after implantation to achieve a lens with the desired optical properties. If the patient's vision needs change due to aging or growth, further refinements can be made months or years later. The changes can be a shift of a fraction of a diopter to several diopters depending on the patient's needs.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The following examples are provided to further illustrate the present invention. The specific limitations set forth in the following examples are intended as illustrative and not limitive.

EXAMPLE 1

A 250 mL round bottom flask was charged with 8.1 g (25 mmol) of 2,7-dibromofluorene, 0.54 g (3.3 mmol) of potassium iodide, 8.4 g (150 mmol) of potassium hydroxide, and 30 mL of DMSO. The flask was cooled to 0° C. and from an addition funnel, 5.5 mL (64 mmol) of allyl bromide was added dropwise. The reaction was allowed to come to room temperature overnight. Next morning, water was added to precipitate out product. The yellow solid was filtered and recrystallized from ethanol to yield 8.2 g (81 % yield) of the 9,9-diallyl-2, 7-dibromofluorene.

A 50 mL round bottom flask was charged with 2.6 g (6.3 mmol) of 9,9-diallyl-2, 7-dibromofluorene, 3.2 g (16 mmol) of 3-methoxydiphenylamine, 1.8 g (19 mmol) of sodium t-butoxide, 0.058 g (0.063 mmol) of tris(dibenzylideneacetone)dipalladium(0), 0.11 g (0.19 mmol) of 1,1-bis(diphenylphosphino)ferrocene, and 60 mL of toluene. The reaction was heated to 93° C. for two days. The solids were filtered off. The filtrate was adhered to silica and purified to yield 0.25 g (6.0% yield) of the two-photon chromophore (2 P).

EXAMPLE 2

A 50 mL round bottom flask was charged with 0.20 g of the two-photon chromophore (2 P), 0.20 g of silicone hydride-crosslinker (XL-H), and 10 mL of toluene. Two drops of "Karsted's" catalyst was added, and the reaction was allowed to stir at room temperature until GC analysis showed the disappearance of the two-photon chromophore. The mixture was passed through activated charcoal to remove the platinum catalyst and the solvent was evaporated off to yield 0.36 g of (XL-2 P).

EXAMPLE 3

A 50 mL round bottom flask was charged with 1.0 g (1.5 mmol) of the two-photon chromophore (2 P), 0.394 g (0.78 mmol) of 1 H, 13 H-tetradecamethylheptasiloxane (H-$L_7$-H), and 10 mL of toluene. Two drops of "Karsted's" catalyst was added, and the reaction was allowed to stir at room temperature until GC analysis showed the disappearance of the two-photon chromophore. The mixture was passed through activated charcoal to remove the platinum catalyst and the solvent was evaporated off to yield 1.1 g (76% yield) of (2 P-$L_7$-2 P).

EXAMPLE 4

A 50 mL round bottom flask was charged with 0.63 g (1.0 mmol) of the two-photon chromophore (2 P), 0.51 g (1.0 mmol) of 1 H, 13 H-tetradecamethylheptasiloxane (H-$L_7$-H), and 10 mL of toluene. Two drops of "Karsted's" catalyst was added, and the reaction was allowed to stir at room temperature until GC analysis showed the disappearance of the two-photon chromophore. The mixture was passed through activated charcoal to remove the platinum catalyst and the solvent was evaporated off to yield 0.76 g (67% yield) of (H-$L_7$-2 P).

EXAMPLE 5

A silicone film was molded by mixing the following:
3.08 g of an methacrylate endcapped silicone macromer (1000 g.$mol^{-1}$), 0.22 g of the 2-photon initiator prepared in Example 3, 0.534 g of a hydride resin crosslinker (3000–5000 g.$mol^{-1}$), 3.50 g of a silicone base polymer (reinforced with silicone resin, LSR-9-part A). The components were mixed thoroughly in a glass mixing vial with a spatula and the mixture was degassed in a desiccator. Subsequently, 3.67 g of a silicone base polymer (reinforced with silicone resin, LSR-9-part B) that contained a Pt-catalyst for a total of 35 ppm was added and mixed thoroughly. The mixture was degassed again to remove any air and the filled into a 1.2 mm thick and 75*75 mm film mold. The film was cured at 37° C. for 24 hours. The film was colorless and optical transparent as measured by UV-Visible spectroscopy.

EXAMPLE 6

The film prepared in Example 5 was irradiated in a microscope designed for 2-photon absorption. The light derived from a Ti:Sapphire laser at 720 nm with a power of 630 mW was focused through an 10× objective with a numerical aperture of 0.30. This gave a 1.2 µm-focused spot for initiation of the 2-photon polymerization. A circular spot with a circumference of ca. 900 µm was irradiated and resulted in a photopolymerized area of this size as shown by the different refraction in the picture below:

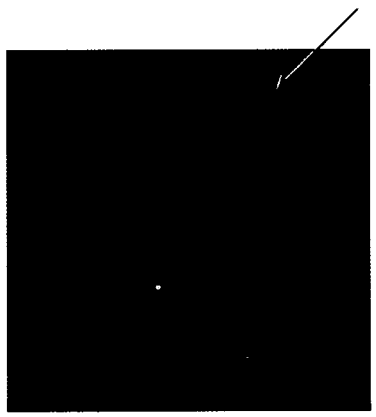

What is claimed is:

1. A photoinitiator having the formula:

A-B-A¹ wherein A and A¹ are independently selected from multiphoton chromophores having the formula

D-π-D wherein D is a tertiary amino electron donor and π is a conjugated bridge and B is a bridging compound comprising an acrylic or siloxane moiety.

2. The photoinitiator of claim 1 wherein B comprises a siloxane moiety having the formula:

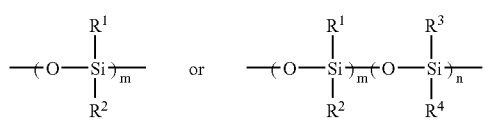

wherein m and n are integers from 1 to 10 and $R^1$, $R^2$, $R^3$ and $R^4$ are independently selected from the group consisting of hydrogen, alkyl, halogenated alkyl, phenyl and aryl.

3. The photoinitiator of claim 1 wherein B comprises an acrylic moiety having the formula:

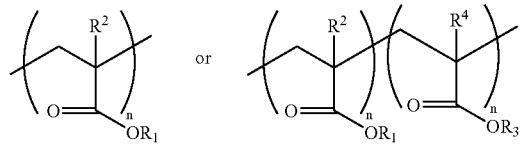

wherein n is an integer ranging from 1 to 10 and $R^1$, $R^2$, $R^3$ and $R^4$ are independently selected from the group consisting of hydrogen, alkyl, substituted alkyl, phenyl and aryl.

4. A photoinitiator having the formula:

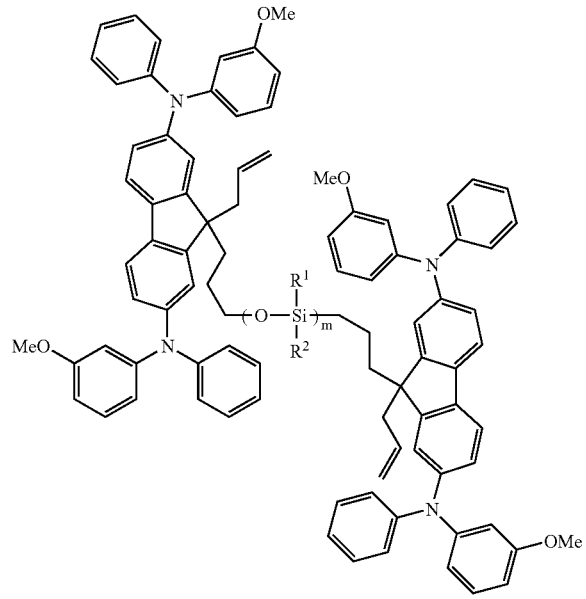

wherein m is an integer from 1 to 10 and $R^1$, $R^2$, $R^3$ and $R^4$ independently selected from the group consisting of hydrogen, alkyl, halogenated alkyl, phenyl and aryl.

5. A light adjustable composition comprising:
a base material;
photopolymerizable macromers;
a photoinitiator, said photoinitiator having the formula:

A-B-A¹ wherein A and A¹ are independently selected from multiphoton chromophores and B is a bridging compound comprising an acrylic or siloxane moiety.

6. The composition of claim 5 wherein the bridging compound is a acrylic moiety having the general formula:

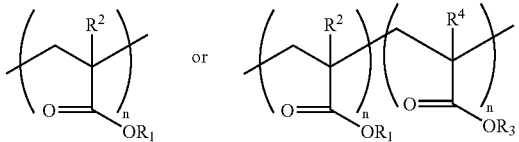

wherein n is an integer from 1 to 10 and $R^1$, $R^2$, $R^3$ and $R^4$ are independently selected from the group consisting of hydrogen, alkyl, substituted alkyl, phenyl and aryl.

7. The composition of claim 5 wherein the bridging compound comprises an siloxane moiety having the formula:

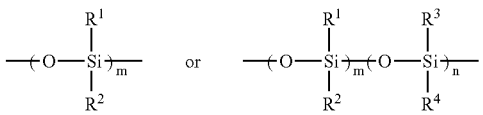

wherein m and n are integers and $R^1$, $R^2$, $R^3$ and $R^4$ are independently selected from the group consisting of hydrogen, alkyl, substituted alkyl, phenyl and aryl.

8. The composition of claim 5 wherein the base material comprises polysiloxane.

9. The composition of claim 5 wherein the base material comprises poly(acrylate).

10. The composition of claim 5 wherein the photoinitiator has the formula:

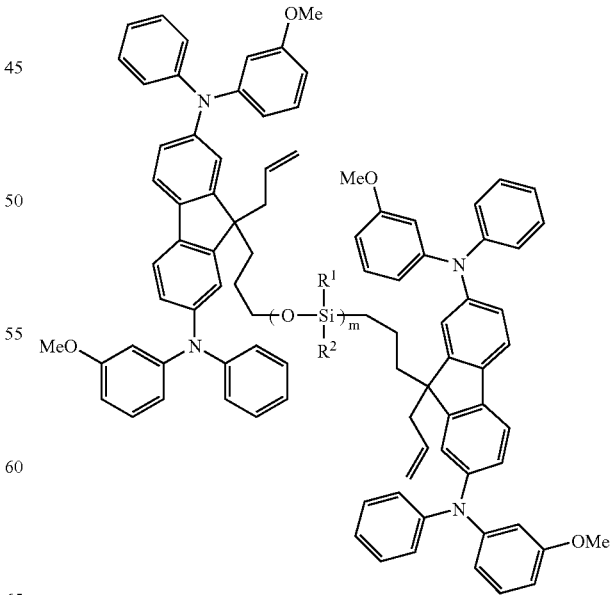

wherein m is an integer from 1 to 10, and $R^1$, $R^2$, $R^3$ and

R[4] independently selected from the group consisting of hydrogen, alkyl, substituted alkyl, phenyl and aryl.

11. The composition of claim 5 wherein the chromophores have the formula:

Dπ-D wherein D is a teritary amino electron donor and π is a conjugated bridge.